(12) United States Patent
Wen

(10) Patent No.: US 7,384,266 B2
(45) Date of Patent: Jun. 10, 2008

(54) METHOD AND APPARATUS FOR MANUFACTURING AND CONSTRUCTING A PHYSICAL DENTAL ARCH MODEL

(75) Inventor: Huafeng Wen, Redwood City, CA (US)

(73) Assignee: Align Technology, Inc., Santa Clara, CA (US)

( * ) Notice: Subject to any disclaimer, the term of this patent is extended or adjusted under 35 U.S.C. 154(b) by 515 days.

(21) Appl. No.: 10/979,823

(22) Filed: Nov. 2, 2004

(65) Prior Publication Data

US 2006/0093992 A1    May 4, 2006

(51) Int. Cl.
    *A61C 11/00*    (2006.01)
(52) U.S. Cl. ...................................... 433/213
(58) Field of Classification Search ............... 433/24, 433/213, 215, 229
    See application file for complete search history.

(56) References Cited

U.S. PATENT DOCUMENTS

| | | | |
|---|---|---|---|
| 4,755,139 A | 7/1988 | Abbatte |
| 4,798,534 A | 1/1989 | Breads |
| 4,856,991 A | 8/1989 | Breads |
| 4,936,862 A | 6/1990 | Walker |
| 5,011,405 A | 4/1991 | Lemchen |
| 5,035,613 A | 7/1991 | Breads |
| 5,055,039 A | 10/1991 | Abbatte |
| 5,059,118 A | 10/1991 | Breads |
| 5,186,623 A | 2/1993 | Breads |
| 5,273,429 A | 12/1993 | Rekow |
| 5,338,198 A | 8/1994 | Wu |
| 5,340,309 A | 8/1994 | Robertson |
| 5,342,202 A | 8/1994 | Deshayes |
| 5,368,478 A | 11/1994 | Andreiko |
| 5,382,164 A | 1/1995 | Stern |
| 5,452,219 A | 9/1995 | Dehoff |
| 5,549,476 A | 8/1996 | Stern |
| 5,587,912 A | 12/1996 | Andersson |
| 5,607,305 A | 3/1997 | Andersson |
| 5,645,421 A | 7/1997 | Slootsky |
| 5,879,158 A | 3/1999 | Doyle |
| 5,975,893 A | 11/1999 | Chishti |
| 6,217,325 B1 | 4/2001 | Chishti |
| 6,227,850 B1 | 5/2001 | Chishti |
| 6,227,851 B1 | 5/2001 | Chishti |
| 6,299,440 B1 | 10/2001 | Phan |
| 6,309,215 B1 | 10/2001 | Phan |
| 6,497,574 B1 | 12/2002 | Miller |
| 6,499,997 B2 | 12/2002 | Chishti |
| 6,514,074 B1 | 2/2003 | Chishti |
| 6,524,101 B1 | 2/2003 | Phan |
| 6,554,611 B2 | 4/2003 | Chishti |
| 6,572,372 B1 | 6/2003 | Phan |
| 6,582,227 B2 | 6/2003 | Phan |
| 6,582,229 B1 | 6/2003 | Miller |

(Continued)

Primary Examiner—Ralph A. Lewis
(74) Attorney, Agent, or Firm—Paul, Hastings, Janofsky & Walker LLP

(57) ABSTRACT

A method produces a physical dental arch model based on a three-dimensional (3D) digital dental arch model. The method includes smoothening the digital dental arch model to make the digital dental arch model suitable for CNC based manufacturing, segmenting the digital dental arch model into at least two manufacturable digital components, producing manufacturable physical components using Computer Numerical Control (CNC) based manufacturing in accordance with the manufacturable digital components, and assembling the manufacturable physical components to form the physical dental arch model.

25 Claims, 9 Drawing Sheets

U.S. PATENT DOCUMENTS

| | | |
|---|---|---|
| 6,602,070 B2 | 8/2003 | Miller |
| 6,607,382 B1 | 8/2003 | Kuo |
| 6,621,491 B1 | 9/2003 | Baumrind |
| 6,626,666 B2 | 9/2003 | Chishti |
| 6,629,840 B2 | 10/2003 | Chishti |
| 6,633,789 B1 | 10/2003 | Nikolskiy |
| 6,665,570 B2 | 12/2003 | Pavloskaia |
| 6,682,346 B2 | 1/2004 | Chishti |
| 6,685,469 B2 | 2/2004 | Chishti |
| 6,685,470 B2 | 2/2004 | Chishti |
| 6,688,886 B2 | 2/2004 | Hughes |
| 6,699,037 B2 | 3/2004 | Chishti |
| 6,705,861 B2 | 3/2004 | Chishti |
| 6,722,880 B2 | 4/2004 | Chishti |
| 6,726,478 B1 | 4/2004 | Isiderio |
| 6,729,876 B2 | 5/2004 | Chishti |
| 6,932,608 B1 * | 8/2005 | Gagliano et al. ........... 433/213 |
| 2007/0077537 A1 * | 4/2007 | Taub et al. ................. 433/213 |

* cited by examiner

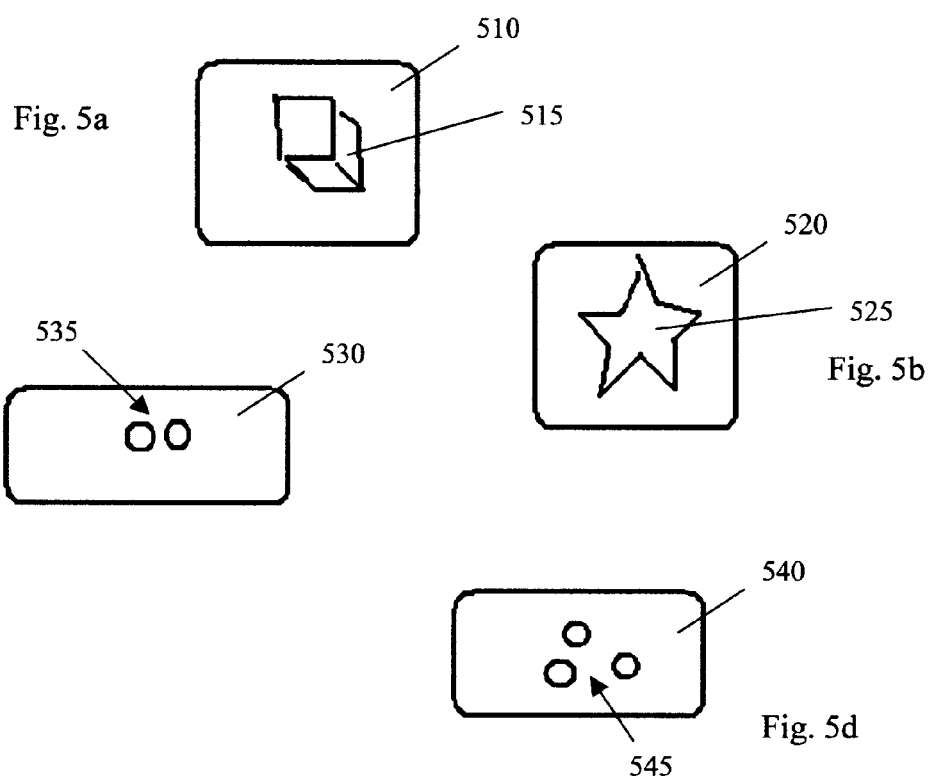

METHOD AND APPARATUS FOR MANUFACTURING AND CONSTRUCTING A PHYSICAL DENTAL ARCH MODEL

TECHNICAL FIELD

This application generally relates to the field of dental care, and more particularly to a system and a method for manufacturing and constructing a physical dental arch model.

CROSS-REFERENCES TO RELATED INVENTIONS

The present invention is related to concurrently filed U.S. Patent Application, titled "Method and apparatus for manufacturing and constructing a dental aligner" by Huafeng Wen, concurrently filed a U.S. Patent Application, titled "Producing an adjustable physical dental arch model" by Huafeng Wen, and concurrently filed U.S. Patent Application, titled "Producing a base for a physical dental arch model" by Huafeng Wen. The disclosure of these related applications are incorporated herein by reference.

BACKGROUND

Orthodontics is the practice of manipulating a patient's teeth to provide better function and appearance. In general, brackets are bonded to a patient's teeth and coupled together with an arched wire. The combination of the brackets and wire provide a force on the teeth causing them to move. Once the teeth have moved to a desired location and are held in a place for a certain period of time, the body adapts bone and tissue to maintain the teeth in the desired location. To further assist in retaining the teeth in the desired location, a patient may be fitted with a retainer.

To achieve tooth movement, orthodontists utilize their expertise to first determine a three-dimensional mental image of the patient's physical orthodontic structure and a three-dimensional mental image of a desired physical orthodontic structure for the patient, which may be assisted through the use of x-rays and/or models. Based on these mental images, the orthodontist further relies on his/her expertise to place the brackets and/or bands on the teeth and to manually bend (i.e., shape) wire, such that a force is asserted on the teeth to reposition the teeth into the desired physical orthodontic structure. As the teeth move towards the desired location, the orthodontist makes continual judgments as to the progress of the treatment, the next step in the treatment (e.g., new bend in the wire, reposition or replace brackets, is head gear required, etc.), and the success of the previous step.

In general, the orthodontist makes manual adjustments to the wire and/or replaces or repositions brackets based on his or her expert opinion. Unfortunately, in the oral environment, it is impossible for a human being to accurately develop a visual three-dimensional image of an orthodontic structure due to the limitations of human sight and the physical structure of a human mouth. In addition, it is humanly impossible to accurately estimate three-dimensional wire bends (with an accuracy within a few degrees) and to manually apply such bends to a wire. Further, it is humanly impossible to determine an ideal bracket location to achieve the desired orthodontic structure based on the mental images. It is also extremely difficult to manually place brackets in what is estimated to be the ideal location. Accordingly, orthodontic treatment is an iterative process requiring multiple wire changes, with the process success and speed being very much dependent on the orthodontist's motor skills and diagnostic expertise. As a result of multiple wire changes, patient discomfort is increased as well as the cost. As one would expect, the quality of care varies greatly from orthodontist to orthodontist as does the time to treat a patient.

As described, the practice of orthodontic is very much an art, relying on the expert opinions and judgments of the orthodontist. In an effort to shift the practice of orthodontic from an art to a science, many innovations have been developed. For example, U.S. Pat. No. 5,518,397 issued to Andreiko, et. al. provides a method of forming an orthodontic brace. Such a method includes obtaining a model of the teeth of a patient's mouth and a prescription of desired positioning of such teeth. The contour of the teeth of the patient's mouth is determined, from the model. Calculations of the contour and the desired positioning of the patient's teeth are then made to determine the geometry (e.g., grooves or slots) to be provided. Custom brackets including a special geometry are then created for receiving an arch wire to form an orthodontic brace system. Such geometry is intended to provide for the disposition of the arched wire on the bracket in a progressive curvature in a horizontal plane and a substantially linear configuration in a vertical plane. The geometry of the brackets is altered, (e.g., by cutting grooves into the brackets at individual positions and angles and with particular depth) in accordance with such calculations of the bracket geometry. In such a system, the brackets are customized to provide three-dimensional movement of the teeth, once the wire, which has a two dimensional shape (i.e., linear shape in the vertical plane and curvature in the horizontal plane), is applied to the brackets.

Other innovations relating to bracket and bracket placements have also been patented. For example, such patent innovations are disclosed in U.S. Pat. No. 5,618,716 entitled "Orthodontic Bracket and Ligature" a method of ligating arch wires to brackets, U.S. Pat. No. 5,011,405 "Entitled Method for Determining Orthodontic Bracket Placement," U.S. Pat. No. 5,395,238 entitled "Method of Forming Orthodontic Brace," and U.S. Pat. No. 5,533,895 entitled "Orthodontic Appliance and Group Standardize Brackets therefore and methods of making, assembling and using appliance to straighten teeth".

Kuroda et al. (1996) Am. J. Orthodontics 110:365-369 describes a method for laser scanning a plaster dental cast to produce a digital image of the cast. See also U.S. Pat. No. 5,605,459. U.S. Pat. Nos. 5,533,895; 5,474,448; 5,454,717; 5,447,432; 5,431,562; 5,395,238; 5,368,478; and 5,139,419, assigned to Ormco Corporation, describe methods for manipulating digital images of teeth for designing orthodontic appliances.

U.S. Pat. No. 5,011,405 describes a method for digitally imaging a tooth and determining optimum bracket positioning for orthodontic treatment. Laser scanning of a molded tooth to produce a three-dimensional model is described in U.S. Pat. No. 5,338,198. U.S. Pat. No. 5,452,219 describes a method for laser scanning a tooth model and milling a tooth mold. Digital computer manipulation of tooth contours is described in U.S. Pat. Nos. 5,607,305 and 5,587,912. Computerized digital imaging of the dental arch is described in U.S. Pat. Nos. 5,342,202 and 5,340,309.

Other patents of interest include U.S. Pat. Nos. 5,549,476; 5,382,164; 5,273,429; 4,936,862; 3,860,803; 3,660,900; 5,645,421; 5,055,039; 4,798,534; 4,856,991; 5,035,613; 5,059,118; 5,186,623; and 4,755,139.

The key to efficiency in treatment and maximum quality in results is a realistic simulation of the treatment process. Today's orthodontists have the possibility of taking plaster models of the upper and lower dental arch, cutting the model into single tooth models and sticking these tooth models into a wax bed, lining them up in the desired position, the so-called set-up. This approach allows for reaching a perfect occlusion without any guessing. The next step is to bond a bracket at every tooth model. This would tell the orthodontist the geometry of the wire to run through the bracket slots to receive exactly this result. The next step involves the transfer of the bracket position to the original malocclusion model. To make sure that the brackets will be bonded at exactly this position at the real patient's teeth, small templates for every tooth would have to be fabricated that fit over the bracket and a relevant part of the tooth and allow for reliable placement of the bracket on the patient's teeth. To increase efficiency of the bonding process, another option would be to place each single bracket onto a model of the malocclusion and then fabricate one single transfer tray per dental arch that covers all brackets and relevant portions of every tooth. Using such a transfer tray guarantees a very quick and yet precise bonding using indirect bonding.

U.S. Pat. No. 5,431,562 to Andreiko et al. describes a computerized, appliance-driven approach to orthodontics. In this method, first certain shape information of teeth is acquired. A uniplanar target arcform is calculated from the shape information. The shape of customized bracket slots, the bracket base, and the shape of the orthodontic archwire, are calculated in accordance with a mathematically-derived target archform. The goal of the Andreiko et al. method is to give more predictability, standardization, and certainty to orthodontics by replacing the human element in orthodontic appliance design with a deterministic, mathematical computation of a target archform and appliance design. Hence the '562 patent teaches away from an interactive, computer-based system in which the orthodontist remains fully involved in patient diagnosis, appliance design, and treatment planning and monitoring.

More recently, Align Technology, Inc. began offering transparent, removable aligning devices as a new treatment modality in orthodontics. In this system, an impression model of the dentition of the patient is obtained by the orthodontist and shipped to a remote appliance manufacturing center, where it is scanned with a CT scanner. A computer model of the dentition in a target situation is generated at the appliance manufacturing center and made available for viewing to the orthodontist over the Internet. The orthodontist indicates changes they wish to make to individual tooth positions. A revised virtual model is provided for the orthodontist to review, until the target situation is agreed upon. A series of removable aligning devices or shells are manufactured and delivered to the orthodontist. The shells will move the patient's teeth to the desired or target position.

U.S. Pat. No. 6,699,037 describes improved methods and systems for repositioning teeth from an initial tooth arrangement to a final tooth arrangement. Repositioning is accomplished with a system comprising a series of appliances configured to receive the teeth in a cavity and incrementally reposition individual teeth in a series of successive steps, usually including at least four successive steps, often including at least ten steps, sometimes including at least twenty-five steps, and occasionally including forty or more steps. Most often, the methods and systems will reposition teeth in from ten to twenty-five successive steps, although complex cases involving many of the patient's teeth may take forty or more steps. The successive use of a number of such appliances permits each appliance to be configured to move individual teeth in small increments, typically less than 2 mm, preferably less than 1 mm, and more preferably less than 0.5 mm. These values refer to the maximum linear translation of any point on a tooth as a result of using a single appliance. The movements provided by successive appliances, of course, will usually not be the same for any particular tooth. Thus, one point on a tooth may be moved by a different distance as a result of the use of one appliance and thereafter moved by a different distance and/or in a different direction by a later appliance.

The individual appliances preferably comprise a polymeric shell having the teeth-receiving cavity formed therein, typically by molding. Each individual appliance is configured so that its tooth-receiving cavity has a geometry corresponding to an intermediate or end tooth arrangement intended for that appliance. That is, when an appliance is first worn by the patient, certain of the teeth will be misaligned relative to an undeformed geometry of the appliance cavity. The appliance, however, is sufficiently resilient to accommodate or conform to the misaligned teeth, and will apply sufficient resilient force against such misaligned teeth in order to reposition the teeth to the intermediate or end arrangement desired for that treatment step.

The fabrication of aligners using a stereo lithography process is disclosed in U.S. Pat. Nos. 6,471,511 and 6,682,346. The stereo lithography process builds the aligner layer by layer, and may use a different aligner mold at each stage of the treatment.

The practice of orthodontics and other dental treatments including preparation of a denture can benefit from a physical dental arch model that is representative of the dentition and the alveolar ridge of a patient to be orthodontically treated. The physical dental arch model, also referred as a physical dental arch model, is often prepared based on an impression model. The physical dental arch model is generally prepared by cutting and arranging individual teeth on the alveolar ridge of the impression model. With this physical dental arch model so prepared, not only is a final goal for the dental treatment made clear, but also the occlusal condition between the maxillary and the mandibular dentitions can be ascertained specifically.

Also, the patient when the physical dental arch model is presented can visually ascertain the possible final result of orthodontic treatment he or she will receive and, therefore, the physical dental arch model is a convenient tool in terms of psychological aspects of the patient.

Making a model for a whole or a large portion of an dental arch is much more difficult than making one tooth abutment for implant purposes. Single teeth do not have the kind of concavities and complexities as in the inter-proximal areas of teeth in an dental arch. Some prior art making the physical dental arch model is carried out manually, involving not only a substantial amount of labor required, but also a substantial amount of time. It is also extremely difficult to machine an accurate dental arch model because of the various complex shapes and the complex features such as inter-proximal areas, wedges between teeth, etc. in a dental arch. There is therefore a long felt need for a practical, effective and efficient methods to produce a physical dental arch model.

SUMMARY OF THE INVENTION

The present invention has been devised to substantially eliminate the foregoing problems and is to provide methods and apparatus to manufacture and construct the physical dental arch model. Implementations of the system may include one or more of the following.

In one aspect, the present invention relates to a method for producing a physical dental arch model based on a three-dimensional (3D) digital dental arch model, comprising:

smoothening the digital dental arch model to make the digital dental arch model suitable for CNC based manufacturing;

segmenting the digital dental arch model into at least two digital components;

producing manufacturable physical components using Computer Numerical Control (CNC) based manufacturing in accordance with the manufacturable digital components; and assembling the physical manufacturable components to form the physical dental arch model.

In another aspect, the present invention relates to a system for producing a physical dental arch model, comprising:

a computer storage device that stores a three-dimensional (3D) digital dental arch model;

a computer processor that can smoothen the digital data in the digital dental arch model and segment the digital dental arch model into at least two manufacturable digital components suitable for CNC based manufacturing; and an apparatus that can produce manufacturable physical components in accordance with the manufacturable digital components, wherein the manufacturable physical components can be assembled to form the physical dental arch model.

In yet another aspect, the present invention relates to a physical dental arch model assembled by a plurality of components, comprising:

two or more manufacturable physical components produced by Computer Numerical Control (CNC) based manufacturing in response to manufacturable digital components segmented from a three-dimensional (3D) digital dental arch model; and a base adapted to receive the manufacturable physical components.

Implementations of the system may include one or more of the following. A method for producing a physical dental arch model based on a three-dimensional (3D) digital dental arch model comprises smoothening the digital dental arch model to make the digital dental arch model suitable for CNC based manufacturing, segmenting the digital dental arch model into at least two manufacturable digital components, producing manufacturable physical components using Computer Numerical Control (CNC) based manufacturing in accordance with the manufacturable digital components and assembling the manufacturable physical components to form the physical dental arch model. The method can further include determining if the smoothened digital dental arch model satisfies one or more predetermine criteria for CNC based manufacturing. The method can further include running a CNC simulator to determine if the smoothened digital dental arch model satisfies one or more predetermine criteria for CNC based manufacturing. The digital dental arch model can include removing sharp gaps and divots in the teeth arch in the digital dental arch model. The manufacturable digital components can include a portion of a tooth, a whole tooth, a plurality of teeth, or a complete teeth arch. The manufacturable digital components and the manufacturable physical components can include features that permit the manufacturable physical components to be assembled into the physical dental arch model. The features can include one or more of a pin, a notch, a protrusion, a hole, an interlocking mechanism, a jig, and a pluggable or an attachable feature.

The method can further include attaching or plugging the manufacturable physical components into each other to form the physical dental arch model. The CNC based manufacturing can includes milling, stereolithography, laser machining, and molding. The physical dental arch model can comprise a material selected from the group consisting of polymers, urethane, epoxy, plastics, plaster, stone, clay, acrylic, metals, wood, paper, ceramics, and porcelain. The method can further include obtaining a cast for a teeth arch from a patient and scanning the cast to obtain the digital data for the digital dental arch model. The method can further include generating a digital model for a base compatible with the digital dental arch model and producing the base that can be assembled with the manufacturable physical components. The base can comprise one or more features to assist the assembling with the manufacturable physical components, said features comprising one or more of a pin, a notch, a protrusion, a hole, an interlocking mechanism, a jig, and a pluggable or attachable feature. The method can further include attaching or plugging the manufacturable physical components into the base to form the physical dental arch model over the base. The method can further include producing the physical base using CNC based manufacturing.

Implementations of the system may include one or more of the following. A system for producing a physical dental arch model comprises a computer storage device that stores a three-dimensional (3D) digital dental arch model; a computer processor that can smoothen the digital data in the digital dental arch model and segment the digital dental arch model into at least two manufacturable digital components suitable for CNC based manufacturing, and an apparatus that can produce manufacturable physical components in accordance with the manufacturable digital components, wherein the manufacturable physical components can be assembled to form the physical dental arch model. The apparatus can produce manufacturable physical components in accordance with the manufacturable digital components using Computer Numerical Control (CNC) based manufacturing. The system can further comprise an apparatus that can produce a physical base that is adapted to receive the manufacturable physical components form the physical dental arch model on the base.

Implementations of the system may include one or more of the following. A physical dental arch model assembled from a plurality of manufacturable physical components, comprises two or more manufacturable physical components produced by Computer Numerical Control (CNC) based manufacturing in response to manufacturable digital components segmented from a three-dimensional (3D) digital dental arch model, and a base adapted to receive the manufacturable physical components. The base can be produced by Computer Numerical Control manufacturing.

Embodiments may include one or more of the following advantages. The present invention provides practical methods and system for making a physical dental arch model. After a digital model of an arch is acquired from a patient, the digital model is first smoothened to remove gaps and divots that cannot be reproduced in a physical model by a machine. The digital dental arch model is then broken down to small manufacturable components that can be readily handled by automated machining such as computer numerical control (CNC) based milling. The manufacturable components can be an individual tooth, multi tooth segment, or a part of a tooth. Features are added to the manufacturable components to allow them to be attached, plugged or locked into each other. The manufacturable physical components manufactured can be assembled to construct a physical dental archphysical dental arch model for various dental applications such as dental crown, dental bridge, aligner fabrication, biometrics, and teeth whitening. The arch model can be assembled from segmented manufacturable components that can individually be manufactured by automated, precise numerical manufacturing techniques.

A further advantage of the present invention is that the manufacturability of the manufacturable components are simulated, verified and refined if necessary prior to manufacturing. As a result, complex arch shapes that cannot be made can now be practically manufactured. Waste and cycle times are reduced in the process from design, testing, pilot, to production.

Simplicity is another advantage of the disclosed system and methods. The manufacturable components can be attached to each other and/or onto a base. The assembled physical dental archphysical dental arch model specifically corresponds to the patient's arch. There is no need for complex and costly mechanisms such as micro-actuators for adjusting multiple degrees of freedom for each tooth component. The described methods and system is simple to make and easy to use.

The manufacturable physical components can be hollow inside and have outer surfaces that allow proper union of the components. The manufacturable physical components can be assembled in pressure forming. The manufacturable physical components can be pre-fabricated similar to LEGO blocks having standard registration and attaching features for assembling. The manufacturable physical components can be automatically assembled by robotic arms under computer control.

Another advantageous feature of the disclosed system and methods is that the manufacturable physical components can be separated, repaired or replaced, and reassembled after the assembly.

The details of one or more embodiments are set forth in the accompanying drawing and in the description below. Other features, objects, and advantages of the invention will become apparent from the description and drawings, and from the claims.

BRIEF DESCRIPTION OF THE DRAWINGS

The accompanying drawing, which are incorporated in and form a part of this specification, illustrate embodiments of the invention and, together with the description, serve to explain the principles of the invention:

FIGS. 5a-d illustrate physical tooth components comprising features that allow them to be plugged or attached into a base.

DESCRIPTION OF INVENTION

Figure 1:
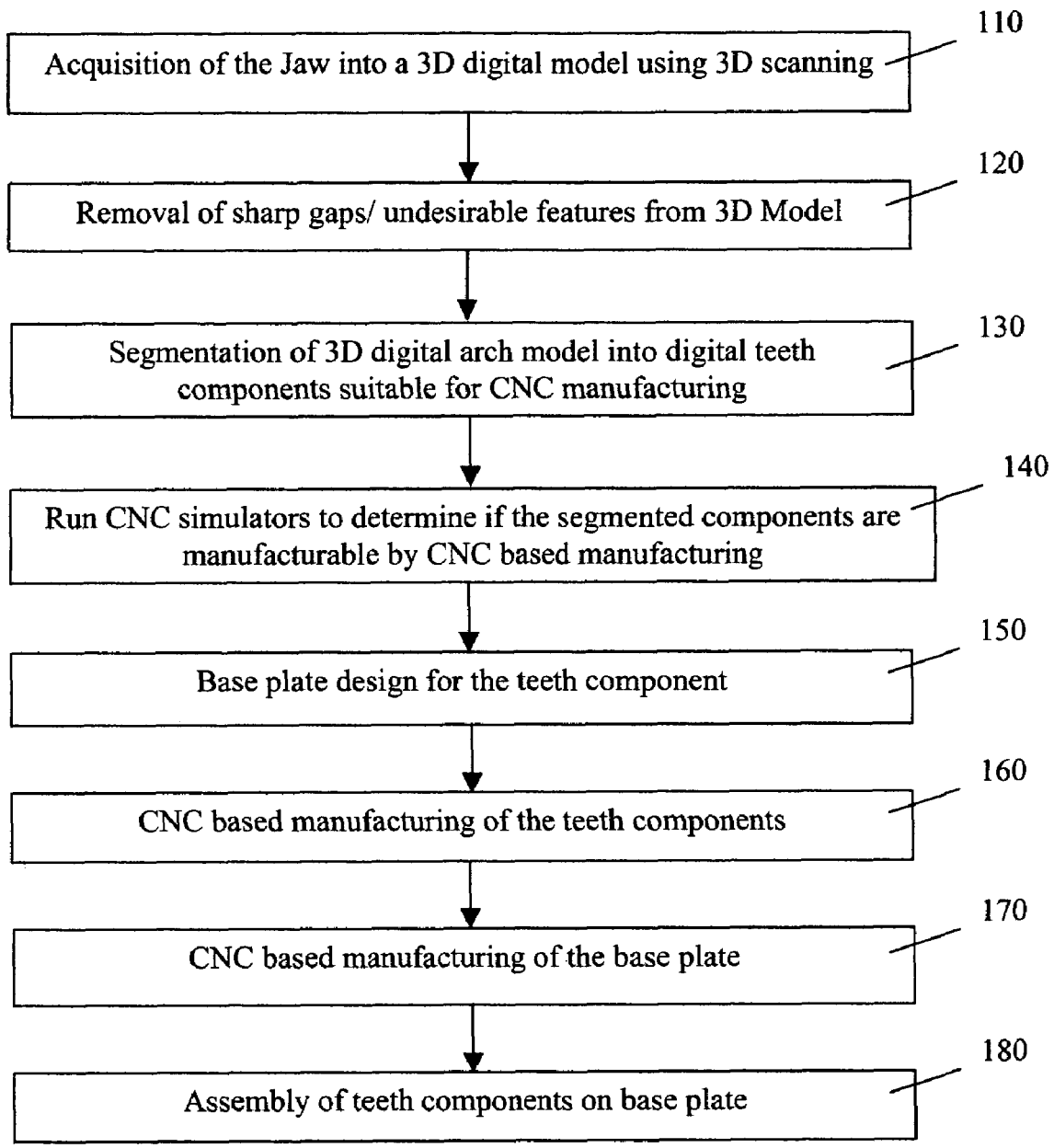
FIG. 1 is a flow chart for producing a physical dental archphysical dental arch model in accordance with the present invention.

A flow chart shown in FIG. 1 illustrates the key steps of producing a physical dental archphysical dental arch model in accordance with the present invention. First, a digital model is acquired from a patient's arch in step 110. The digital model is three dimensional and can be obtained by 3D scanning of a cast produced from the patient's arch. The digital model includes a mesh of points in three dimensions that define the surfaces of an entire or a large portion of an upper or lower arch. Details of obtaining a digital model of an arch are disclosed in above referenced and currently filed U.S. patent application Ser. No. titled "Producing a base for a physical dental archphysical dental arch model" by Huafeng Wen, the content of which is incorporated herein by reference.

Next, in step 120, the digital dental arch model is smoothened by computer processing. A software takes the digital dental arch model as input. One or more criteria for the degree of smoothness can also be provided by a user. Undesirable features such as sharp gaps and divots are removed from the digital dental arch model.

The criteria for the degree of smoothness can be required by the specific dental applications. The plastic aligners for example cannot reach into the gaps between the teeth. In addition, it is also undesirable to have aligner to have fine features inside the gaps because that could potentially create resistance to desired tooth movement in an orthodontics treatment procedure.

The criteria for the degree of smoothness can also be required by type of the tools used to manufacture the physical components as described below. In the present invention, Computer Numerical Control or CNC based manufacturing refers to the automated and computer controlled machining. The most basic function of a CNC machine is automatic, precise, and consistent motion control. All forms of CNC equipment have two or more directions of motion, called axes. These axes can be precisely and automatically positioned along their lengths of travel. The two most common axis types are linear (driven along a straight path) and rotary (driven along a circular path). Instead of causing motion by manually turning cranks and handwheels as is required on conventional machine tools, CNC machines allow motions to be actuated by servomotors under control of the CNC, and guided by the part program. Generally speaking, the motion type (rapid, linear, and circular), the axes to move, the amount of motion and the motion rate (feed rate) are programmable with almost all CNC machine tools.

In the present invention, in addition to CNC based milling, the CNC based manufacturing is also compatible with other computer numerical controlled manufacturing processes such as stereolithography, laser machining, and molding. Other examples of CNC based manufacturing include CNC based milling, Laminated Object Manufacturing, Selective Laser Sintering, Fused Deposition Modeling, Solid Ground Curing, 3D ink jet printing.

For manufacturing a physical dental archphysical dental arch model, however, the drill bit in CNC based milling is usually too big to reach into the gaps and holes in a teeth arch model. CNC milling is usually around one axis, which makes it difficult to machine the complex shapes within the gaps between teeth. CNC based milling also has limitations in accuracy and repeatability between different stages of milling.

Several techniques have been used to remove the gaps in the digital dental arch model to produce a smoothened digital dental arch model:

1. Boolean union with primitive 3D objects. Graphics Constructive Solid Geometry primitives or self developed predefined geometries can be inserted into the gaps in the digital dental arch model and then combine with the original 3D digital mesh.

2. Extrusion. The surfaces near the gaps are extruded to fill the gaps in the original 3D digital mesh.

3. Geometry modification by moving vertices. Sharp gaps can be closed by specifying the desired boundaries and modifying the mesh to the desired boundaries in the problem regions.

4. Subdivision of surfaces and movement. Similar to Technique 3, the arch surfaces are subdivided in the regions of surface modification for greater smoothness and continuity.

5. Convex hull creation of sub parts to be used as filling objects in the gaps. The gap regions are first located and the points defining edges of the sharp gaps are identified. A convex hull is computed based on these points. The convex hull is joined with the original mesh to fill the gaps using Boolean union.

6. Using parametric surfaces to model fill objects that will be used fit in the gaps.

Figure 2:
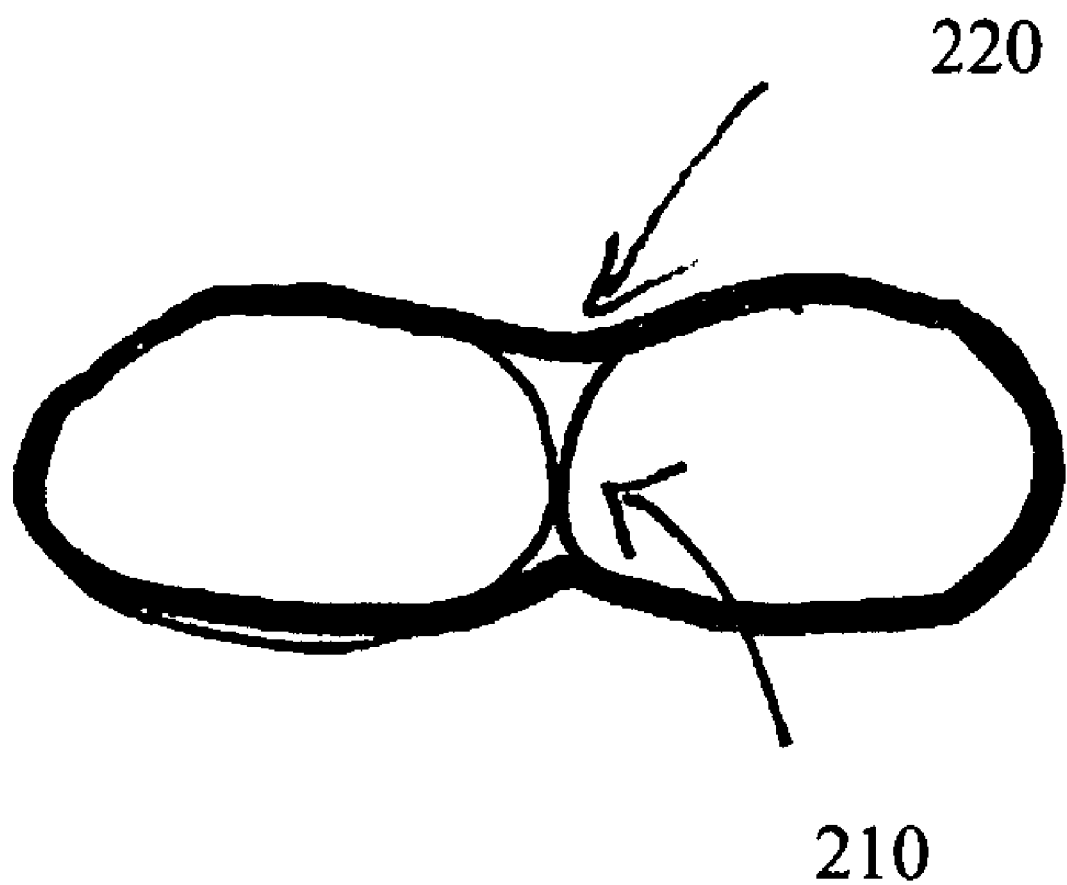
FIG. 2 illustrates the smoothening of the digital dental arch model in preparation for a CNC based manufacturing of physical dental archphysical dental arch model in accordance with the present invention.

FIG. 2 illustrates the smoothening effects of the gap filling by comparing the surfaces 210 of before gap fillings and the surfaces 220 after the gap fillings.

A simulation can be conducted using the smoothened the digital dental arch model as input to check and verify the smoothness of the digital dental arch model. The simulation can be run using a simulator software in response to the smoothness criteria required by the manufacturing process such as CNC based milling or the dental applications. Refinement ad smoothening iterations may be called for if the smoothness criteria are not completely satisfied.

Figure 3:
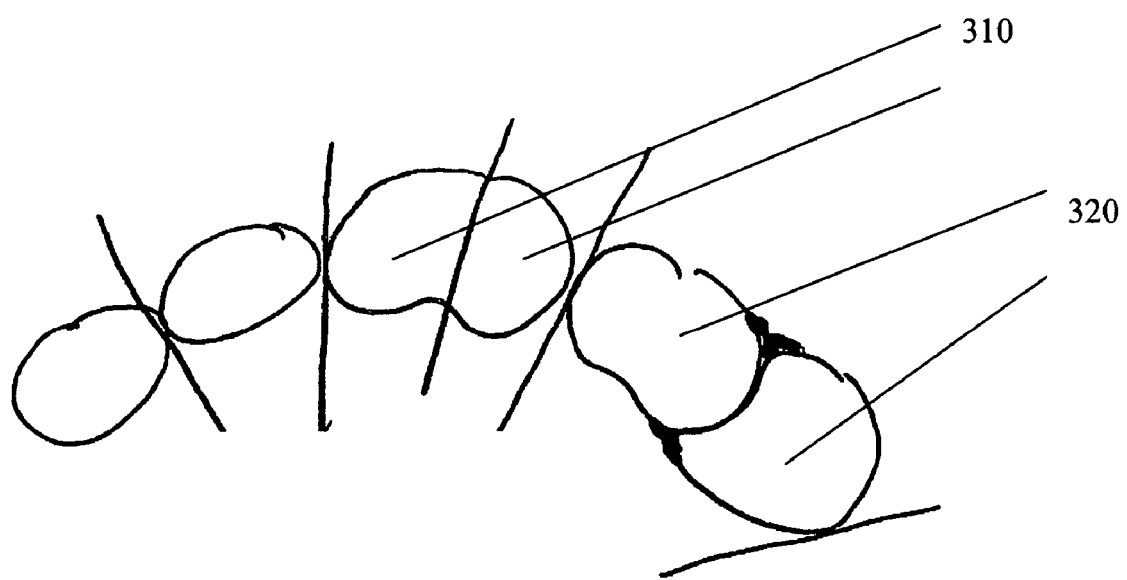
FIG. 3 illustrates the segmentation of digital dental arch model into segmented components suitable for CNC based manufacturing in accordance with the present invention.

Next, in Step 130, the smoothened digital dental arch model is segmented into manufacturable digital components suitable for CNC manufacturing. A typical arch in the digital dental arch model includes a whole upper or lower arch or a portion of an arch comprising a plurality of teeth. As shown in FIG. 3, the physical components can be a portion of a tooth 310, a whole individual tooth 320, or sometimes a segment of teeth arch including several teeth.

The criteria for the size, location, and the number of physical components are based on both orthodontic needs and manufacturing requirements. The orthodontic criteria require the tracking of how the original locations of the physical components and which components can be moved together as a group, which physical components must be moved independently, and which teeth cannot be moved.

The manufacturing requirements relate mainly to the manufacturability of the digital components, which usually supersedes the orthodontic criteria. For example, a single tooth can be divided into multiple components to make its model manufacturable. The segmented digital components can be evaluated by a simulator software to verify their manufacturability by a specific manufacture process such as CNC based milling, which may suggest refinement in the size, location, and numbers of the segmentation. The simulation can also include an evaluation and estimation of the physical strength after the assembly, as described below, to determine if the assembled physical components are strong enough to withstand the physical forces in a pressure forming process.

In one embodiment, the smoothening of the digital dental arch model may occur during the segmentation. Different segmented digital components may receive different types or degree of smoothening so that the smoothening is tailored to the segments and manufacturing requirements.

An advantage of the present invention is that an arch model is segmented to small manufacturable components that can be manufactured by automated, precise numerical manufacturing techniques.

A further advantageous feature of the present invention is that the manufacturability of the digital components are simulated, verified and refined if necessary prior to manufacturing (Step 140). As a result, complex arch shapes that cannot be made can now be practically manufactured. Waste and cycle times are reduced in the process from design, testing, pilot, to production.

Figure 4A:
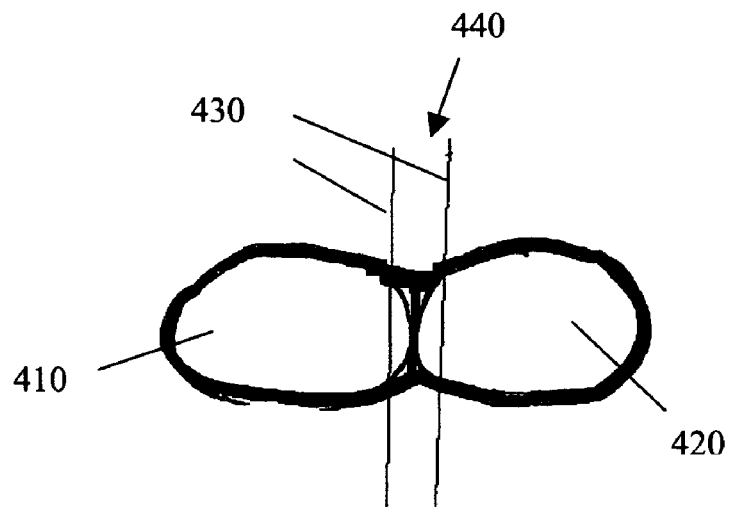
FIGS. 4a-4d illustrate the segmentation of an inter-proximal region by removing a space around the inter-proximal region and replacing it by a wedge.
Figure 4B:
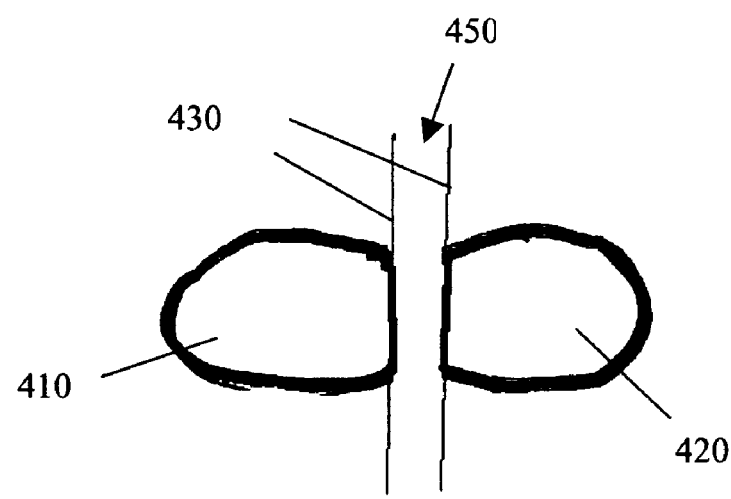

In another embodiment, special care needs to be applied to the inter-proximal regions in segmenting arch into digital components. In many cases, the inter-proximal regions involve such complexity and details that CNC based manufacturing such as cutting or milling cutting can result in losing details. As shown in FIGS. 4a and 4b, an inter-proximal region 440 is removed between a tooth model 410 and a tooth model 420 along the lines 430. This can be achieved over tooth models in a tooth arch model by using a CNC machine, or by data processing over the digital dental arch model. A thin gap 450 is formed between tooth model 410 and tooth model 420.

Figure 4C:
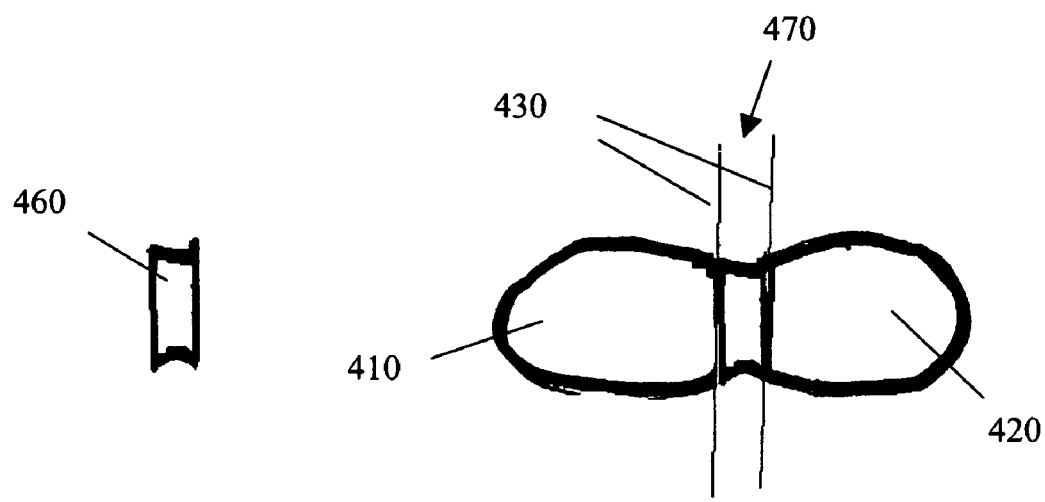
Figure 4D:
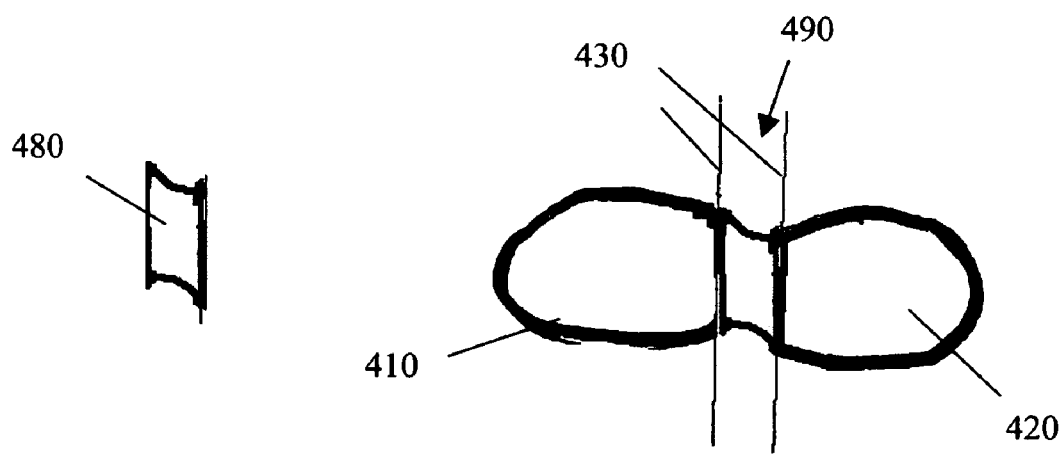

A wedge 460, shown in FIG. 4c, is then first designed using proprietary Wedge design software and then made using CNC based manufacturing technique. The wedge 470 can be inserted into the gap 450 to complete the digital tooth arch model or the physical tooth arch model. The wedge making and insertion can take into account of the movement of the tooth models 410, 420 during the orthodontic treatment. As shown FIG. 4d, the wedge 480 is made to be slightly sheared. The wedge 490 inserted between the tooth models 410, 420 can therefore induce a relative movement between the tooth models 410, 420. In general the relative movement can include translational and directional adjustment in different degrees of freedoms. The resulted tooth arch model can then be used to made dental aligners.

FIGS. 5a, 5b, 5c and 5d illustrate examples of the manufacturable physical components 510,520,530,540 that respectively include features 515,525,535,545 that allow them to be attached to each other in order to form a whole or part of a physical dental archphysical dental arch. FIG. 5a shows a feature 515 having a cubic base for a physical component 510. FIG. 5b shows a feature 525 having a star-shaped base for a physical component 520. The star-shaped base defines unique orientation when physical component 520 is assembled with another physical component. FIGS. 5c and 5d show features 535 and 545 respectively comprising two and three pins in the physical components 530 and 540. The two pins ensure uniquely defined orientation when physical component 530 is assembled with another physical component. Similarly, the three pins in feature 545 ensure unique configuration when physical component 540 is assembled with another physical component.

In general, the physical components may include features such as a pin, a registration slot, a notch, a protrusion, a hole, an interlocking mechanism, a jig, and a pluggable or an attachable feature. The adjacent manufactured manufacturable physical components may include matching male (e.g. mushroom, push pins) and female features (e.g. hole, notches etc.) for attachment. The male and female features can be fabricated for example by casting mold that include female and male matching features in the mold, each responsible for making respective male and female features. The adjacent manufacturable physical components can attached together by simply pushing male feature into the female feature, for example, by pressing a pushpin into a receiving hole.

The physical components can be labeled with unique identifications, and assembled and detached in predetermined sequences. The assembling and detachment can be automated by for example a robotic arm under the control of a computer in accordance with the predetermined sequences.

Figure 6:
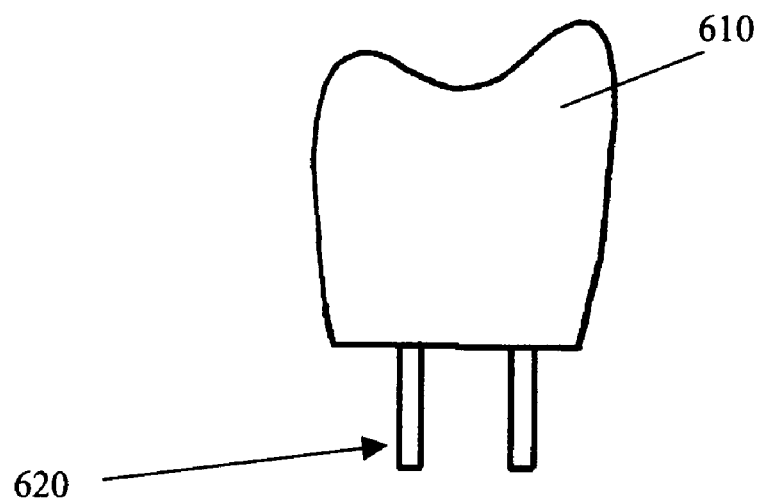
FIG. 6 illustrates how a tooth component fits into a base component.

The manufacturable physical components 610 (FIG. 6) can include a feature 620 that allow it to be attached or plugged to a based plate. The manufacturable physical components 630 can also include two pins 620 for attaching to a base.

Figure 7:
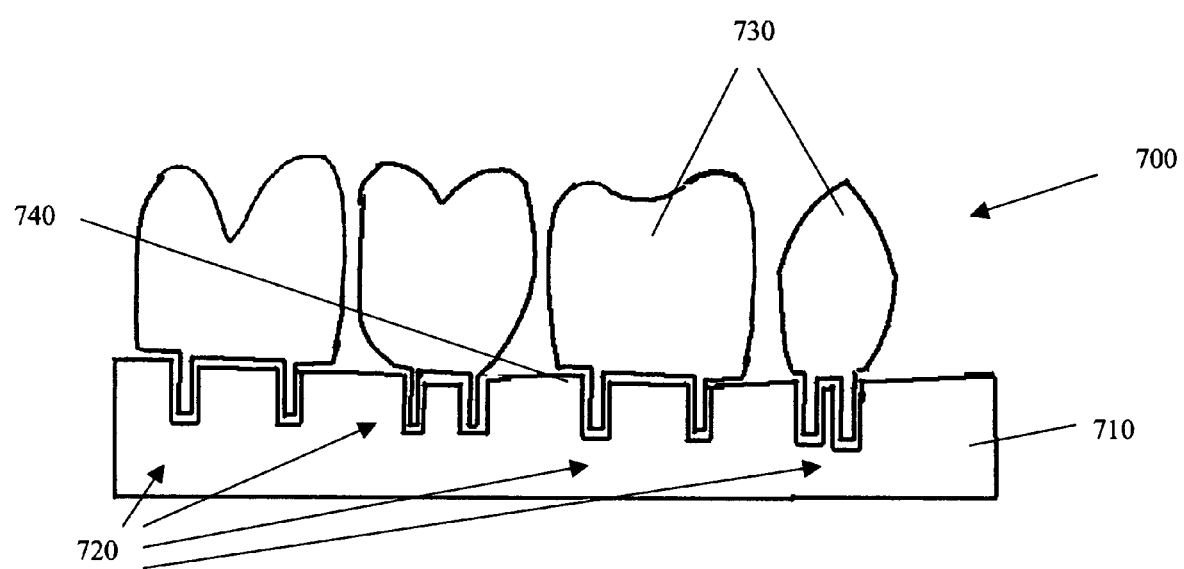
FIG. 7 illustrates exemplified arrangements for fitting one or more physical tooth components into a base.

The manufacturable physical components 730 can be assembled over the base 710 to form a physical dental archphysical dental arch model 700 as shown in FIG. 7. The base 710 is designed in Step 150 for the manufacturable components 730. The base 710 comprises one or more features 720 which are adapted to receive the features 740 of the manufacturable physical components 730 for assembling of the physical dental archphysical dental arch model 700. The features 720 receiving the manufacturable components 730 guarantee unique positions and orientations for manufacturable components 730 in the final physical dental archphysical dental arch model 700. The features 720 can include a pin, a notch, a protrusion, a hole, an interlocking mechanism, a jig, and a pluggable or attachable feature. All or a subset of the manufacturable physical components 730 (Step 160) can be attached to the base 710. For example, the manufacturable physical components 730 (Step 160) can be readily plugged attached to slots prepared on the base 710.

Features 720 and features 740 are designed to be fit each other, which for example, can include matching notches and pins. The features 720 and features 740 can be selected in software designs from predefined structures and then add to the root direction of the manufacturable components 610, 730 and the top of the base 710. Alternatively, features 720 and features 740 can be designed in software and finished by a combination of manufacturing (Steps 160,170) and assembling (Step 180). For example, both features 720 and features 740 can be notches or holes. A pin can be plugged into the notches to assemble the manufacturable components 730 and the top of the base 710. Features 720 and features 740 can include asymmetric shapes such as an asymmetric star to ensure a unique orientation in the fitting between the base 710 and the manufacturable components 730.

In one embodiment, the manufacturable components are assembled in pressure forming. The manufacturable physical components may be hollow inside and have outer surfaces that match the manufacturable digital components to allow proper union of the manufacturable physical components.

In another embodiment, the manufacturable physical components can be pre-fabricated similar to LEGO blocks. The surfaces of the manufacturable physical components may include standard registration and attaching features for them to join together. The LEGO-like manufacturable physical components can be automatically assembled by robotic arms under computer control.

In yet another embodiments, the manufacturable physical components can be separated and repaired after the assembly. The attaching features between manufacturable physical components allow the components to be detached in a sequence. Broken component can be removed, repaired or replaced, followed by re-assembling.

The manufacturable physical components 610,730 are manufactured in Step 160 using CNC based manufacturing techniques. The segmented manufacturable digital components are provided to as input files to a CNC machine. The manufacturable physical components 610,730 are manufactured individually. In the disclosed methods and systems, the precision and yield of the CNC based manufacturing are high because manufacturability has been considered and verified as part of the designs of the manufacturable components. Common materials for the manufacturable components include polymers, urethane, epoxy, plastics, plaster, stone, clay, acrylic, metals, wood, paper, ceramics, and porcelain.

The physical dental archphysical dental arch model may optionally include a base on which teeth components can be attached. The base 710 is next manufactured in Step 170. In accordance with the present invention, the base 710 can be designed to possess smooth surfaces so that it complies with CNC manufacturing requirements. The CNC based manufacturing of the base 710 can include the use of a prefabricated base part and precision drilling of notches on the prefabricated base part to define features 720. The positions of the manufacturable components 710 can then be precisely defined in the physical dental archphysical dental arch model 700.

Finally, the physical dental archphysical dental arch model 700 is constructed in Step 180 by assembling the manufacturable physical components 730 and the base 710. The manufacturable physical components 730 can also be assembled onto the base 710 in different arrangements such as one pin and two pins as illustrated in FIG. 7. The joining features at the base can also include a registration slot, a notch, a protrusion, a hole, an interlocking mechanism, and a jig. In another arrangement, only even numbered teeth can be plugged into the base while the odd numbered teeth are slot in between the even numbered teeth from their sides.

The physical dental archphysical dental arch model 700 can be used in different dental applications such as dental crown, dental bridge, aligner fabrication, biometrics, and teeth whitening. For aligner fabrication, for example, each stage of the teeth treatment may correspond a unique physical dental arch model. Aligners can be fabricated using different physical dental arch models one at a time as the teeth movement progresses during the treatment. At each stage of the treatment, the desirable teeth positions for the next stage are calculated. A physical dental arch model having modified teeth positions is fabricated using the process described above. A new aligner is made using the new physical dental arch model.

In accordance with the present invention, each base is specific to an arch configuration. There is no need to reconfigure or manipulate a multiple of degrees of freedom for each manufacturable component once it is plugged into the base. The described methods and system have the advantages of being simple to make and easy to use.

Figure 8:
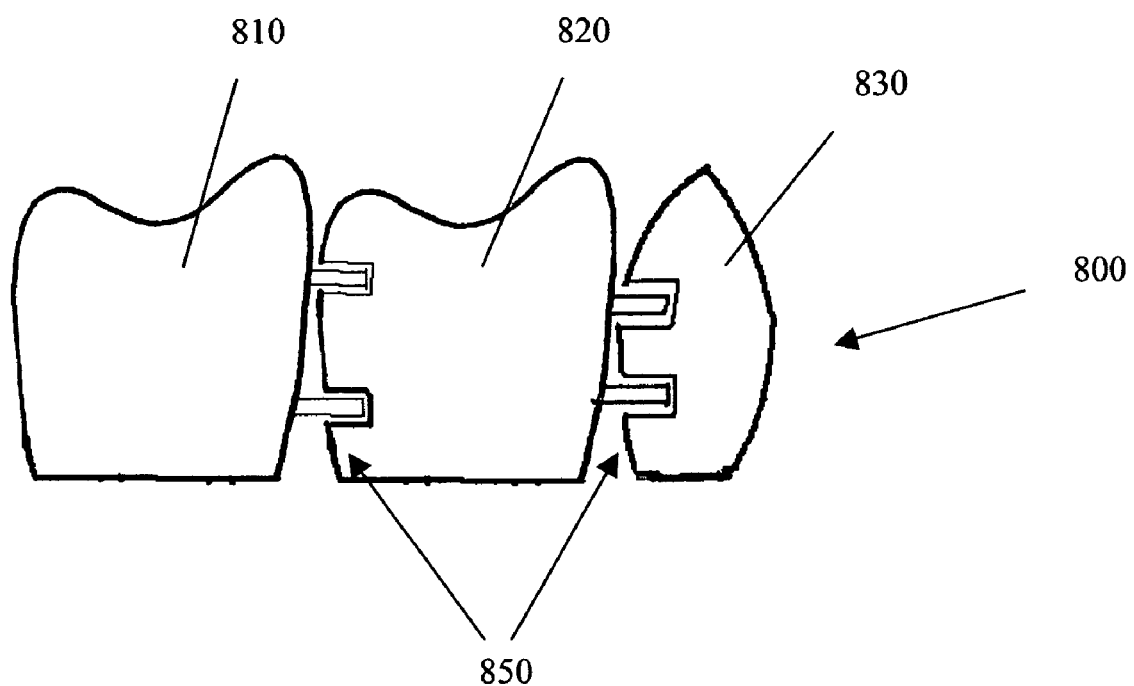
FIG. 8 illustrates a portion of an arch assembled by a plurality of physical tooth components each comprising features that assist the attachment to attach to each other to form a physical dental archphysical dental arch model without a base.

In another embodiment, as shown in FIG. 8, the different physical components 810,820,830 can be assembled to form a whole or a portion of a physical dental arch model 800 without a base. The different physical components 810,820, 830 can be attached or plugged into each other at joining features 850 that can be pins, registration slot, a notch, etc.

The described methods and system are also economic. Different stages of the physical dental arch model can share the same manufacturable physical components. Only a new base having new set of receptive positions for the manufacturable physical components are required for each stage of the treatment. The manufacturable physical components can be reused through the treatment process. The positions for the manufacturable physical components at each stage of the treatment can be modeled using an orthodontic treatment software.

Although specific embodiments of the present invention have been illustrated in the accompanying drawings and described in the foregoing detailed description, it will be understood that the invention is not limited to the particular embodiments described herein, but is capable of numerous rearrangements, modifications, and substitutions without departing from the scope of the invention. The following claims are intended to encompass all such modifications.

What is claimed is:

1. A method for producing a physical dental arch model based on a three-dimensional (3D) digital dental arch model, comprising:
    smoothening the digital dental arch model to make the digital dental arch model suitable for CNC based manufacturing;
    segmenting the digital dental arch model into at least two manufacturable digital components;
    producing manufacturable physical components using Computer Numerical Control (CNC) based manufacturing in accordance with the manufacturable digital components; and
    assembling the manufacturable physical components to form the physical dental arch model.

2. The method of claim 1, further comprising:
    determining if the smoothened digital dental arch model satisfies one or more predetermine criteria for CNC based manufacturing.

3. The method of claim 2, further comprising running a CNC simulator to determine if the smoothened digital dental arch model satisfies one or more predetermine criteria for CNC based manufacturing.

4. The method of claim 1, wherein smoothening the digital dental arch model includes removing sharp gaps and divots in the teeth arch in the digital dental arch model.

5. The method of claim 1, wherein the manufacturable digital components include a portion of a tooth, a whole tooth, a plurality of teeth, or a complete teeth arch.

6. The method of claim 1, wherein the manufacturable digital components and the manufacturable physical components include features that permit the manufacturable physical components to be assembled into the physical dental arch model.

7. The method of claim 1, wherein the features include one or more of a pin, a notch, a protrusion, a hole, an interlocking mechanism, a jig, and a pluggable or an attachable feature.

8. The method of claim 1, further comprising attaching or plugging the manufacturable physical components into each other to form the physical dental arch model.

9. The method of claim 1, wherein the CNC based manufacturing includes milling, stereolithography, laser machining, and molding.

10. The method of claim 1, wherein the physical dental arch model comprises a material selected from the group consisting of polymers, urethane, epoxy, plastics, plaster, stone, clay, acrylic, metals, wood, paper, ceramics, and porcelain.

11. The method of claim 1, further comprising:
    obtaining a cast for a teeth arch from a patient; and
    scanning the cast to obtain the digital data for the digital dental arch model.

12. The method of claim 1, further comprising:
    generating a digital model for a base compatible with the digital dental arch model; and
    producing the base that can be assembled with the manufacturable physical components.

13. The method of claim 12, wherein the base comprises one or more features to assist the assembling with the manufacturable physical components, said features comprising one or more of a pin, a notch, a protrusion, a hole, an interlocking mechanism, a jig, and a pluggable or attachable feature.

14. The method of claim 12, further comprising attaching or plugging the manufacturable physical components into the base to form the physical dental arch model over the base.

15. The method of claim 12, further comprising:
    producing the physical base using CNC based manufacturing.

16. A system for producing a physical dental arch model based on a three-dimensional (3D) digital dental arch model, comprising:
    a computer configured to smoothen a digital dental arch model to make the digital dental arch model suitable for Computer Numerical Control (CNC) based manufacturing, the computer further configured to segment the digital dental arch model into at least two manufacturable digital components and to provide CNC information for manufacturing the at least two manufacturable digital components; and
    a manufacturing machine receiving the CNC information, wherein the manufacturing machine is configured to produce manufacturable physical components using CNC based manufacturing in accordance with the CNC information, wherein the manufacturable physical components are configured to be assembled into a physical dental arch model.

17. The system of claim 16, wherein the computer is further configured to determine if the smoothened digital dental arch model satisfies one or more predetermined criteria for CNC based manufacturing.

18. The system of claim 17, wherein the computer comprises a CNC simulator that determines if the smoothened digital dental arch model satisfies one or more predetermine criteria for CNC based manufacturing.

19. The system of claim 16, wherein the computer is configured to remove one or more sharp gaps and divots in a teeth arch in the digital dental arch model.

20. The system of claim 16, wherein the manufacturable digital components include a portion of a tooth, a whole tooth, a plurality of teeth, or a complete teeth arch.

21. The system of claim 16, wherein the manufacturable digital components and the manufacturable physical components include features that permit the manufacturable physical components to be assembled into the physical dental arch model, including one or more of a pin, a notch, a protrusion, a hole, an interlocking mechanism, a jig, and a pluggable or an attachable feature.

22. The system of claim 16, wherein the manufacturing machine is configured to perform one or more of milling, stereolithography, laser machining, and molding.

23. The system of claim 16, wherein the physical dental arch model comprises a material selected from the group consisting of polymers, urethane, epoxy, plastics, plaster, stone, clay, acrylic, metals, wood, paper, ceramics, and porcelain.

24. The system of claim 16, wherein the computer is further configured to generate a digital model for a base compatible with the digital dental arch model, wherein the base comprises one or more features to facilitate assembling with the manufacturable physical components, said features comprising one or more of a pin, a notch, a protrusion, a hole, an interlocking mechanism, a jig, and a pluggable or attachable feature.

25. The system of claim 24, wherein the computer is configured to provide CNC information for manufacturing the base.

* * * * *